United States Patent [19]

Vilani

[11] 4,282,233

[45] Aug. 4, 1981

[54] ANTIHISTAMINIC 11-(4-PIPERIDYLIDENE)-5H-BENZO-[5,6]-CYCLOHEPTA-[1,2-B]-PYRIDINES

[75] Inventor: Frank J. Vilani, West Caldwell, N.J.

[73] Assignee: Schering Corporation, Kenilworth, N.J.

[21] Appl. No.: 160,795

[22] Filed: Jun. 19, 1980

[51] Int. Cl.³ .................. A61K 31/445; C07D 401/04
[52] U.S. Cl. ....................................... 424/267; 546/93
[58] Field of Search .......................... 546/93; 424/267

[56] References Cited

U.S. PATENT DOCUMENTS

| | | | |
|---|---|---|---|
| 3,326,924 | 6/1967 | Villani | 546/93 |
| 3,357,986 | 12/1967 | Villani | 546/93 |
| 3,366,635 | 1/1968 | Villani | 546/93 |
| 3,419,565 | 12/1968 | Villani | 546/93 |

OTHER PUBLICATIONS

Villani, F., et al., *J. Med. Chem.*, 15 (7), 750–754 (1972).

*Primary Examiner*—Richard A. Schwartz
*Attorney, Agent, or Firm*—Paul H. Ginsburg

[57] ABSTRACT

11-(4-Piperidylidene)-5H-benzo-[5,6]-cyclohepta-[1,2-b]-pyridines and their 5,6-dihydro derivatives are disclosed. The compounds are useful as antihistamines with little or no sedative effects.

13 Claims, No Drawings

ANTIHISTAMINIC 11-(4-PIPERIDYLIDENE)-5H-BENZO-[5,6]-CYCLOHEPTA-[1,2-B]-PYRIDINES

The present invention relates to novel 11-(4-piperidylidene)-5H-benzo-[5,6]-cyclohepta-[1,2-b]-pyridines.

U.S. Pat. No. 3,326,924 discloses 6,11-dihydro-11-(N-methyl-4-piperidylidene)-5H-benzo-[5,6]-cyclohepta-[1,2-b]-pyridine and 11-(N-methyl-4-piperidylidene-5H-benzo-[5,6]-cyclohepta-[1,2-b]-pyridine, useful as antihistamines.

The compounds of the present invention are likewise useful as antihistamines, but are preferred to the compounds of the aforementioned patent because the present compounds have little or no sedative effects, thus being preferred for use with patients that must operate machinery or automobiles or perform other mental or physical tasks requiring a high level of concentration.

The compounds of the present invention are compounds of the formula

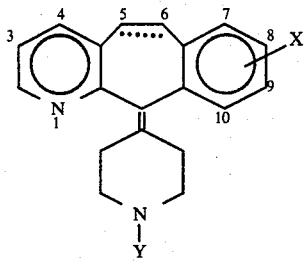

wherein the dotted line represents an optional double bond and wherein the numbering system used herein is illustrated. In this formula, X is hydrogen or halo and Y is substituted carboxylate or substituted sulfonyl for example Y is —COOR or $SO_2R$, with the proviso that when Y is —COOR, R is $C_1$ to $C_{12}$ alkyl, substituted $C_1$ to $C_{12}$ alkyl, phenyl, substituted phenyl, $C_7$ to $C_{12}$ phenyl alkyl, $C_7$ to $C_{12}$ phenyl alkyl wherein the phenyl moiety is substituted or R is -2,-3, or -4 piperidyl or N-substituted piperidyl wherein the substituents on said substituted $C_1$ to $C_{12}$ alkyl are selected from amino or substituted amino and the substituents on said substituted amino are selected from $C_1$ to $C_6$ alkyl, the substituents on said substituted phenyl and on said substituted phenyl moiety of the $C_7$ to $C_{12}$ phenyl alkyl are selected from $C_1$ to $C_6$ alkyl and halo, and the substituent on said N-substituted piperidyl is $C_1$ to $C_4$ alkyl; and with the proviso that when Y is $SO_2R$, R is $C_1$ to $C_{12}$ alkyl, phenyl, substituted phenyl, $C_7$ to $C_{12}$ phenyl alkyl, $C_7$ to $C_{12}$ phenyl alkyl wherein the phenyl moiety is substituted, wherein the substituents on said substituted phenyl and said substituted phenyl moiety of the $C_7$ to $C_{12}$ phenyl alkyl are selected from $C_1$ to $C_6$ alkyl and halo.

In a preferred embodiment of the present invention, Y is —COOR and R is $C_1$ to $C_6$ alkyl or substituted alkyl, phenyl, substituted phenyl, $C_7$ to $C_{12}$ aralkyl or substituted aralkyl or -2, -3 or -4 piperidyl or N-substituted piperidyl. When R is substituted alkyl, R is substituted with amino or with substituted amino. The substituents on said substituted amino are $C_1$ to $C_6$ alkyl. The substituents on the aforementioned substituted phenyl and on the phenyl moiety of the substituted aralkyl are preferably $C_1$ to $C_6$ alkyl or halo.

In a second preferred embodiment of the present invention, Y is $SO_2R$ and R is $C_1$ to $C_6$ alkyl, phenyl, substituted phenyl, $C_7$ to $C_{12}$ aralkyl or substituted aralkyl, wherein the substituents on said substituted phenyl and on the phenyl moiety of the substituted aralkyl are $C_1$ to $C_6$ alkyl or halo.

The aforementioned alkyl groups may be linear, branched or cyclic or may contain both cyclic and linear or cyclic and branched moieties. Halo may be fluoro, chloro, bromo or iodo.

The present invention also relates to a pharmaceutical composition comprising an effective amount of a compound of the formula I as defined above, together with a pharmaceutically acceptable carrier and to a method of effecting an anti-allergic response in an animal comprising administering to the animal an effective amount of a compound of the formula I as defined above.

Generally, compounds of the present invention are prepared by replacing a methyl or another replacable substituent, for example carbophenoxy on the nitrogen of the piperidylidene ring of an appropriate compound of the formula I with the desired substituent.

For example, compounds of the formula I wherein Y is —COOR are prepared by reacting a compound of the formula I wherein Y is methyl (Compound IA) or an appropriate derivative of Compound IA with an appropriate chloroformate, for example, an alkylchloroformate or phenyl chloroformate in order to replace the N-methyl group on the piperidylidene group of Compound IA.

Compounds of the formula I wherein Y is —COOR may also be prepared by reacting a compound of the formula I wherein Y is —COOR and R is phenyl with the sodium salt of an appropriate alcohol.

Compounds of the formula I wherein Y is —COOR and R is tert-butyl may be prepared by reacting a compound of the formula I wherein Y is hydrogen with a di-tertiarybutyl carbonate in an inert solvent, for example, tetrahydrofuran.

Compounds of the formula I wherein Y is —$SO_2R$ are prepared by reacting a compound of the formula I wherein Y is hydrogen with a compound of the formula Cl—$SO_2R$, wherein R has the same value as R in the desired product, in the presence of an excess of anhydrous potassium carbonate in an inert solvent, for example dry toluene.

The following non-limiting Examples further illustrate the preparation of the compounds of the present invention:

EXAMPLE 1

A.

11-(N-Carboethoxy-4-piperidylidene)-6,11-dihydro-5H-benzo-[5,6]-cyclohepta-[1,2-b]-pyridine To a solution of 10.9 g (0.1 mole) of ethylchloroformate in 300 ml. of anhydrous benzene is added dropwise, with stirring at room temperature, a solution of 14.5 g (0.05 M) of 11-(N-methyl-4-piperidylidene)-6,11-dihydro-5H-benzo-[5,6]-cyclohepta-[1,2-b]-pyridine (Compound IA) in 200 ml of benzene. The solution is stirred and is heated under reflux overnight (16–20 hrs.). The mixture is cooled and is poured into ice water and the organic layer is separated, washed with water, dried, and then concentrated to dryness. The residue is triturated with petroleum ether and a white solid having a melting point of 106°–107° C. is recrystallized from isopropyl ether after decolorization with decolorizing carbon.

B.

11-(N-Carboethoxy-4-piperidylidene)-8-chloro-6,11-dihydro-5H-benzo-[5,6]-cyclohepta-[1,2-b]-pyridine Using the procedure of Example IA, react 16.2 g of the 8-chloro derivative of Compound IA and 10.9 g (0.1 mole) of ethylchloroformate to prepare the title compound, having a melting point of 128°–130° C. The 7,9 and 10-chloro analogues are similarly prepared.

C.

11-(N-Carbomethoxy-4-piperidylidene)-6,11-dihydro-5H-benzo-[5,6]-cyclohepta-[1,2-b]-pyridine Using the procedure of Example IA, react 14.5 g of Compound IA and 9.4 g of methylchloroformate to prepare the title compound, having a melting point of 116°–118° C.

EXAMPLE 2

11-(N-Carbophenoxy-4-piperidylidene)-6,11-dihydro-5H-benzo-[5,6]-cyclohepta-[1,2-b]-pyridine (Compound IB)

To a solution of 29.1 g (0.1 mole) of Compound IA in 150 ml. of anhydrous carbon tetrachloride is added 17 g of phenylchloroformate in an equal volume of anhydrous carbontetrachloride. Heat under reflux for 15 minutes with stirring and pour into water. Separate and wash the organic layer with water and remove solvent. Extract the residue with ether, filter off the insoluble material and remove the ether. The residue is recrystallized from isopropyl ether to yield the title compound having a melting point of 127°–130° C.

Similarly prepare the 7,8,9, or 10-chloro derivatives of the title compound using this procedure:

EXAMPLE 3

11-(N-Carboisopropoxy-4-piperidylidene)-6,11-dihydro-5H-benzo-[5,6]-cyclohepta-[1,2-b] pyridine Dissolve 0.5 g sodium metal in 50 ml isopropanol and add 7.9 g of Compound IB from Example 2. Heat with stirring for 5 hours on the steam bath at 90°–95° and allow to cool overnight.

Add ice water to precipitate the product and extract 3 times with ether and once with chloroform. Wash with water, distill off solvents, triturate with hexane and recrystallize from isopropylether. The melting point is 147°–148° C.

Using this procedure and replacing the isopropanol with n-butanol, cyclopentanol, allylalcohol, cyclopropylmethanol, benzylalcohol, p-chlorobenzylalcohol, phenethylalcohol, dimethylaminoethylalcohol or N-methyl-4-hydroxy piperidine prepare the corresponding carbamoyl derivatives. Similarly, using the chloro derivatives of Compound IB and the sodium salts of the aforementioned alcohols, prepare the chloro derivatives of the aforementioned carbamoyl derivatives.

EXAMPLE 4

11-(N-Carbo-t-butoxy-4-piperidylidene)-6,11-dihydro-5H-benzo-[5,6]-cyclohepta-[1,2-b]-pyridine.

Dissolve 13.8 g of 11-(4-piperidylidene)-6,11 dihydro-5H-benzo-[5,6]-cyclohepta-[1,2-b]-pyridine (Compound IC) prepared according to Villani et. al., J. Med. Chem. 15, 750 (1972) in 250 ml of dry tetrahydrofuran. With stirring, add in one portion 12 g of di-t-butyl carbonate and stir at room temperature overnight. The mixture is poured into water, is extracted with ether, is washed with water and the solvent removed. Recrystallize the residue from isopropyl ether. The melting point is 144°–145° C.

EXAMPLE 5

11-(N-Methanesulfonyl-4-piperidylidene)-6,11-dihydro-5H-benzo-[5,6]-cyclohepta-[1,2-b]-pyridine.

To 10 g of Compound IC in 200 ml of dry toluene add 13 g of anhydrous potassium carbonate. After several minutes of stirring at room temperature, add dropwise a solution of 6 g of methanesulfonyl chloride in 20 ml of toluene. Continue stirring for 16 to 20 hours and then filter. Recrystallize the solid material from ethanol. The melting point is 223°–224° C.

Using this procedure and adjusting the weight of the requisite sulfonyl chloride so that 0.04 moles of said alkanesulfonyl chloride are used, the ethanesulfonyl, n-propylsulfonyl, n-butylsulfonyl, cyclopropylsulfonyl, heptylsulfonyl, dodecylsulfonyl, phenylsulfonyl, p-methylphenyl-sulfonyl, p-fluorophenylsulfonyl, p-chlorophenylsulfonyl, benzylsulfonyl, p-chlorobenzylsulfonyl, p-tertbutylphenylsulfonyl and cyclopentylsulfonyl compounds of formula I wherein Y is $SO_2R$ are obtained.

Similarly, prepare the tricyclic ring substituted chloro derivatives.

Substituting the appropriate starting material having a double bond between the 5 and 6 positions of the ring system, and using the procedures set forth in Examples 1 to 5 above for the corresponding 6,11-dihydro compounds, the corresponding 6,11-dehydro compounds are prepared. Also, by substituting the appropriate bromo or other halo analogue, as desired, of the chloro compounds of the Formula I used as starting materials, the desired halo compounds of the formula I are prepared.

The compounds of the present invention are useful as non-sedating antihistamines. These compounds act as anti-allergic agents in the treatment of such conditions as perennial and seasonal allergic rhinitis and chronic urticaria.

The compounds of the present invention are administered in pharmaceutical formulations comprising the compound in admixture with a pharmaceutical carrier suitable for enteral or parenteral administration. The formulations may be in solid form, as for example tablets and capsules, or in liquid form as for example syrups, elixirs, emulsions, and injectables. In the formulation of pharmaceutical dosage forms there generally is utilized excipients as for example, water, gelatin, lactose, starches, magnesium stearate, talc, vegetable oils, benzyl alcohols, gums, polyalkylene glycols, and petroleum jelly. Preferred formulations are more fully illustrated in Example 6.

Although the required dosage will be determined by such factors as the patient's age, sex, weight and the severity of the allergic reaction to be treated, the preferred human dosage range is likely to be 4 to 50 mg of the effective compound 1 to 3 times per day. The preferred dosage ranges for other animals can readily be determined by using standard testing methods.

The following Examples are illustrative of the aforementioned pharmaceutical compositions:

EXAMPLE 6

A syrup comprising a compound of the present invention (Active Compound) is prepared from the following ingredients:

|  | per ml |
| --- | --- |
| Active Compound | 0.100 mg |
| Sucrose | 600 mg |
| Sorbitol | 140 mg |
| Propylene Glycol | 20.0 mg |
| Methylparaben | 1.00 mg |
| Propylparaben | 0.200 mg |
| F.D. & C. Yellow No. 6 | 0.225 mg |
| Alcohol USP | 0.0021 ml |
| Limitation Black Currant Flavor | 0.001 ml |
| Purified Water USP | q.s. |
|  | 1.0 ml |

The syrup is prepared by combining the above ingredients according to standard techniques.

EXAMPLE 7

A tablet comprising a compound of the present invention (Active Compound) is prepared by a spray-dry process from the following ingredients:

| Component I | mg/tablet |
| --- | --- |
| Active Compound | 1.00 |
| Lactose, Hydrous USP (Impalpable Powder) | 212 |
| Polyvinylpyrrolidine Povidone NF | 10.0 |
| Corn Starch (Food Grade) | 15.0 |
| Purified Water USP (Evaporates) | 0.102 ml |
| Additional Components |  |
| Corn Starch (Food Grade) | 11.5 |
| Magnesium Stearate USP | 0.500 |

The materials of Component I are combined and spray dried by standard techniques. The resulting spray dried material is combined with the additional components listed above and processed to form tablets.

I claim:

1. A compound of the formula

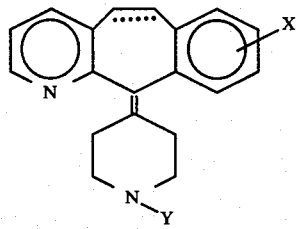

(I)

wherein the dotted line represents an optional double bond; X is hydrogen or halo; and wherein Y is —COOR or $SO_2R$; with the proviso that when Y is —COOR, R is $C_1$ to $C_{12}$ alkyl, substituted $C_1$ to $C_{12}$ alkyl, phenyl, substituted phenyl, $C_7$ to $C_{12}$ phenylalkyl, $C_7$ to $C_{12}$ phenylalkyl wherein the phenyl moiety is substituted or R is -2,-3, or -4 piperidyl or N-substituted piperidyl wherein the substituents on said substituted $C_1$ to $C_{12}$ alkyl are selected from amino or substituted amino and the substituents on said substituted amino are selected from $C_1$ to $C_6$ alkyl, the substituents on said substituted phenyl and on said substituted phenyl moiety of the $C_7$ to $C_{12}$ phenylalkyl are selected from $C_1$ to $C_6$ alkyl and halo, and the substituent on said N-substituted piperidyl is $C_1$ to $C_4$ alkyl; and with the proviso that when Y is $SO_2R$, R is $C_1$ to $C_{12}$ alkyl, phenyl, substituted phenyl, $C_7$ to $C_{12}$ phenylalkyl, $C_7$ to $C_{12}$ phenylalkyl wherein the phenyl moiety is substituted, wherein the substituents on said substituted phenyl and said substituted phenyl moiety of the $C_7$ to $C_{12}$ phenylalkyl are selected from $C_1$ to $C_6$ alkyl and halo.

2. A compound according to claim 1, wherein Y is —COOR, wherein R is as defined in claim 1, said compound having a single bond between the 5- and 6-carbons.

3. A compound according to claim 1, wherein Y is —$SO_2R$, wherein R is as defined in claim 1, said compound having a single bond between the 5- and 6-carbons.

4. A compound according to claim 2, wherein X is hydrogen, said compound having a single bond between the 5- and 6-carbons.

5. A compound according to claim 2, wherein X is 8-chloro, said compound having a single bond between the 5- and 6-carbons.

6. A compound according to claim 3, wherein X is hydrogen, said compound having a single bond between the 5- and 6-carbons.

7. 11-(N-carboethoxy-4-piperidylidene)-8-chloro-6,11-dihydro-5H-benzo-[5,6]-cyclohepta-[1,2-b]-pyridine.

8. 11-(N-methanesulfonyl-4-piperidylidene)-6,11-dihydro-5H-benzo-[5,6]-cyclohepta-[1,2-b]-pyridine.

9. 11-(N-carboethoxy-4-piperidylidene)-6,11-dihydro-5H-benzo-[5,6]-cyclohepta-[1,2-b]-pyridine.

10. 11-(N-carbomethoxy-4-piperidylidene)-6,11-dihydro-5H-benzo-[5,6]-cyclohepta-[1,2-b]-pyridine.

11. 11-(N-carbophenoxy-4-piperidylidene)-6,11-dihydro-5H-benzo-[5,6]-cyclohepta-[1,2-b]-pyridine.

12. An antihistaminic pharmaceutical composition comprising an effective amount of a compound as claimed in any one of claims 1–10 and a pharmaceutically acceptable carrier.

13. A method of effecting an anti-allergic response in an animal comprising administering to the animal an effective amount of a compound as claimed in any one of claims 1 to 11.

* * * * *

UNITED STATES PATENT AND TRADEMARK OFFICE
CERTIFICATE OF CORRECTION

PATENT NO. : 4,282,233
DATED : August 4, 1981
INVENTOR(S) : Frank J. Villani

It is certified that error appears in the above-identified patent and that said Letters Patent are hereby corrected as shown below:

ON THE TITLE PAGE:

Change inventor's name from "Frank J. Vilani" to

-- Frank J. Villani --.

Signed and Sealed this

*Twenty-fourth* Day of *November 1981*

[SEAL]

*Attest:*

GERALD J. MOSSINGHOFF

*Attesting Officer*  *Commissioner of Patents and Trademarks*

UNITED STATES PATENT AND TRADEMARK OFFICE

Certificate

Patent Number: 4,282,233            Patented: August 4, 1981

On petition requesting issuance of a certificate of correction of inventorship pursuant to 35 U.S.C. 256, it has been found that the above-identified patent, through error and without any deceptive intent, improperly sets forth the inventorship. Accordingly, it is hereby certified that the correct inventorship of this patent is:
Frank J. Villani and Charles V. Magatti.

Signed and Sealed This Twenty-Sixth Day of December, 1989

MARY C. LEE

*Supervisory Patent Examiner*
*Patent Examing Group 120*
*Art Unit 121*
*Organic Chemistry*

UNITED STATES PATENT AND TRADEMARK OFFICE

CERTIFICATE EXTENDING PATENT TERM
UNDER 35 U.S.C. § 156

PATENT NO.:     4,282,233

DATED:          August 4, 1981

INVENTORS:      Frank J. Villani et al.

PATENT OWNER:   Schering Corporation

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

2 YEARS with all rights pertaining thereto as provided by 35 U.S.C. § 156(b).

I have caused the seal of the Patent and Trademark Office to be affixed this 20th day of September 1994.

Bruce A. Lehman
Assistant Secretary of Commerce and
Commissioner of Patents and Trademarks

REEXAMINATION CERTIFICATE (4145th)
United States Patent [19]
Villani et al.

[11] B1 4,282,233
[45] Certificate Issued  Sep. 5, 2000

[54] ANTIHISTAMINIC 11-(4-PIPERIDYLIDENE)-5H-BENZO[5,6]-CYCLOHEPTA-[1,2]-PYRIDINES

[75] Inventors: Frank J. Villani, West Caldwell; Charles V. Magatti, Verona, both of N.J.

[73] Assignee: Schering Corporation, Kenilworth, N.J.

Reexamination Request:
No. 90/005,324, Apr. 9, 1999

Reexamination Certificate for:
Patent No.: 4,282,233
Issued: Aug. 4, 1981
Appl. No.: 06/160,795
Filed: Jun. 19, 1980

Certificate of Correction issued Nov. 24, 1981.

[51] Int. Cl.$^7$ ............... A61K 31/4545; A61P 37/08; C07D 401/02
[52] U.S. Cl. ............................. 514/290; 546/93

[56] References Cited

PUBLICATIONS

Casy, A.F., "Chemistry of Anti–H$_1$ Histamine Antagonists," (Roche e. Silva M. ed.) *Histamine II and Anti–Histaminics*, Springer–Verlag Berlin Heidelberg New York, 1978, pp. 175–214.

Kirk–Othmer "Encyclopedia of Chemical Technology" Second Edition, vol. 16, pp. 640–679 (1968).

Kupchan et al., "Drug Latentiation. III. Labile Amide Derivatives of Normeperidine," *J. Med. Chem.*, 10:960–961 (1967).

Protiva, M., "Recent Progress on the Pharmaco–Chemical Research on Antihistamine Drugs and Psychotropic Agents—Derivatives of Tricyclic Systems Having a Seven– or Eight–Membered Middle Ring," *Farmaco, Ed. sci.*, 21:76–104 (1966).

Villani et al., "Derivatives of 10, 11–Dihydro–5H–dibenzo [a,d] cycloheptene and Related Compounds. 6. Aminoalkyl Derivatives of the Aza Isosteres," *J. Med. Chem.*, 15(7):750–754 (1972).

Villani et al., "Benzopyranopyridine Derivatives. 1. Aminoalkyl Derivatives of the Azaxanthenes as Bronchodilating Agents," *J. Med. Chem.*, 18(1):1–8 (1975).

Witiak, et al., "Absorption, Distribution, Metabolism, and Elimination of Antihistamines," contained in *Histamine II and Anti–Histaminics* cited in C1, pp. 513–560.

*Primary Examiner*—Robert W. Ramsuer

[57] ABSTRACT

11-(4-Piperidylidene)-5H-benzo-[5,6]-cyclohepta-[1,2-b]-pyridines and their 5,6-dihydro derivatives are disclosed. The compounds are useful as antihistamines with little or no sedative effects.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–13 is confirmed.

* * * * *